(12) United States Patent
Igarashi

(10) Patent No.: US 12,208,190 B2
(45) Date of Patent: Jan. 28, 2025

(54) BIOLOGICAL COMPONENT SEPARATION DEVICE

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 750 days.

(21) Appl. No.: 17/415,409

(22) PCT Filed: Dec. 24, 2019

(86) PCT No.: PCT/JP2019/050484
§ 371 (c)(1),
(2) Date: Jun. 17, 2021

(87) PCT Pub. No.: WO2020/138024
PCT Pub. Date: Jul. 2, 2020

(65) Prior Publication Data
US 2022/0040392 A1     Feb. 10, 2022

(30) Foreign Application Priority Data
Dec. 25, 2018   (JP) ................................ 2018-240924

(51) Int. Cl.
*A61M 1/36*   (2006.01)
*A61M 1/02*   (2006.01)

(52) U.S. Cl.
CPC ........ *A61M 1/3636* (2014.02); *A61M 1/0218* (2014.02)

(58) Field of Classification Search
CPC .............. A61M 1/3636; A61M 1/0218; A61M 2207/00
See application file for complete search history.

(56) References Cited

U.S. PATENT DOCUMENTS 6,129,853 A * 10/2000 Sasayama ........... A61M 1/3633
                                                   210/791
6,221,264 B1 * 4/2001 Ishida ................. A61M 1/3633
                                                   604/408
(Continued)

FOREIGN PATENT DOCUMENTS

EP           2554190         2/2013
JP      H06327768 A   *   11/1994
(Continued)

OTHER PUBLICATIONS

Yokono, JPH07328113A, English machine translation (Year: 1995).*
(Continued)

*Primary Examiner* — Dirk R Bass
(74) *Attorney, Agent, or Firm* — Sheridan Ross P.C.

(57) ABSTRACT

A biological component separation device includes a device main body which is formed of a soft material in a sheet-like shape and in which a filter accommodating unit is provided, a filter member, an introduction port member, and a lead-out port member. An introduction line and a lead-out line are provided in the device main body. In a state in which the device main body is suspended by an introduction tube, a filter accommodating unit inlet where the filter accommodating unit and the introduction line are connected is positioned lower than a filter accommodating unit outlet where the filter accommodating unit and the lead-out line are connected.

17 Claims, 8 Drawing Sheets

(56) References Cited

U.S. PATENT DOCUMENTS

| | | | | |
|---|---|---|---|---|
| 2005/0133439 | A1* | 6/2005 | Blickhan | B29C 66/81431 |
| | | | | 210/489 |
| 2007/0043317 | A1* | 2/2007 | Sugawara | A61M 1/3633 |
| | | | | 604/406 |

FOREIGN PATENT DOCUMENTS

| | | | | |
|---|---|---|---|---|
| JP | 07328113 A | * | 12/1995 | |
| JP | H11-216179 | | 8/1999 | |
| WO | WO 2005/032619 | | 4/2005 | |
| WO | WO 2011/125617 | | 10/2011 | |
| WO | WO-2017142003 A1 | * | 8/2017 | ....... A61B 5/150251 |
| WO | WO 2018/230155 | | 12/2018 | |
| WO | WO-2018230155 A1 | * | 12/2018 | ............ A61M 1/025 |

OTHER PUBLICATIONS

Sasaki, JPH06327768A, English machine translation (Year: 1994).*
International Search Report and Written Opinion for International (PCT) Patent Application No. PCT/JP2019/050484, dated Apr. 7, 2020, 7 pages.
Official Action (with English translation) for Japan Patent Application No. 2021-519910, dated May 16, 2023, 9 pages.

* cited by examiner

BIOLOGICAL COMPONENT SEPARATION DEVICE

TECHNICAL FIELD

The present invention relates to a biological component separation device that separates a predetermined biological component from a biological fluid.

For example, in International Publication No. WO 2010/026891, a blood separation device is disclosed that separates a predetermined blood component (for example, white blood cells) from blood collected from a blood donor. Such a blood separation device is equipped with a housing, a filter member that partitions the housing into a first chamber and a second chamber, an introduction port member provided at one end portion of the housing, and a lead-out port member provided at another end portion of the housing. An interior hole of the introduction port member communicates with the first chamber, and an interior hole of the lead-out port member communicates with the second chamber.

SUMMARY OF INVENTION

In the case of using the above-described blood separation device, a blood bag which contains the blood prior to being separated and the introduction port member of the blood separation device are connected to each other via an introduction tube, and together therewith, an accommodating bag for accommodating the blood component after being separated and the lead-out port member of the blood separation device are connected to each other via a lead-out tube.

Thereafter, a priming operation of the blood separation device is performed. More specifically, the user suspends the blood bag on a suspension platform, and retains the blood separation device in an up/down inverted state so as to position the lead-out port member upwardly together with positioning the introduction port member downwardly. Consequently, due to the difference in elevation, the blood flows into the housing from the blood bag and via the introduction port member, together with air inside the housing being discharged from the lead-out port member.

When the priming operation is completed, in a state in which the blood separation device is suspended by the introduction tube so that the introduction port member is positioned upwardly together with the lead-out port member being positioned downwardly, the blood which is introduced from the blood bag into the blood separation device due to the difference in elevation is filtered by the filter member. In this manner, with the above-described blood separation device, when the priming operation is carried out, it is necessary to turn the blood separation device upside down, which is considered troublesome.

The present invention has been devised in consideration of the aforementioned problem, and has the object of providing a biological component separation device, which with a simple and economical configuration, is capable of automatically performing a priming operation.

One aspect of the present invention is characterized by a biological component separation device that separates a predetermined biological component from a biological fluid, the biological component separation device comprising a device main body formed of a soft material in a sheet-like shape, a filter member configured to partition an internal space of a filter accommodating unit provided in the device main body into a first chamber and a second chamber, and to capture the predetermined biological component, an introduction port member disposed in the device main body and configured to introduce the biological fluid, and a lead-out port member disposed in the device main body and configured to deliver out the biological fluid, wherein the device main body is provided with an introduction line interconnecting the first chamber and the introduction port member, and a lead-out line interconnecting the second chamber and the lead-out port member, and in a state in which the device main body is suspended, a filter accommodating unit inlet where the filter accommodating unit and the introduction line are connected is positioned lower than a filter accommodating unit outlet where the filter accommodating unit and the lead-out line are connected.

Another aspect of the present invention is characterized by a biological component separation device that separates a predetermined biological component from a biological fluid, the biological component separation device comprising a device main body formed of a soft material in a sheet-like shape, a filter member configured to partition an internal space of a filter accommodating unit, which is provided in the device main body and is equipped with a fluid inlet and a fluid outlet, into a first chamber and a second chamber, and to capture the predetermined biological component, an introduction port unit disposed in the device main body and configured to introduce the biological fluid, a lead-out port unit disposed in the device main body and configured to deliver out the biological fluid, a first line connecting the fluid inlet provided in the first chamber and the introduction port unit, and a second line connecting the fluid outlet provided in the second chamber and the lead-out port unit, wherein the fluid inlet of the first chamber and the lead-out port unit are positioned so as to face each other, and the fluid outlet of the second chamber and the introduction port unit are positioned so as to face each other.

According to the one aspect of the present invention, in the state in which the device main body is suspended, since the filter accommodating unit inlet is positioned lower than the filter accommodating unit outlet, the priming operation can be performed automatically without turning the device main body upside down. More specifically, in the state in which the device main body is suspended, by the biological fluid that is introduced from the introduction line into the filter accommodating unit via the filter accommodating unit inlet that is positioned downwardly, it is possible for the air inside the filter accommodating unit to be discharged into the lead-out line via the upwardly positioned filter accommodating unit outlet. Further, since the introduction line and the lead-out line are provided in the device main body which is formed in a sheet-like shape, the biological component separation device can be manufactured at a lower cost in comparison with a case in which the introduction line, the lead-out line, and the device main body are molded separately. Accordingly, it is possible for the biological component separation device to be constituted in a simple and economical manner.

According to the other aspect of the present invention, the fluid inlet of the first chamber and the lead-out port unit are positioned so as to face each other, and the fluid outlet of the second chamber and the introduction port unit are positioned so as to face each other. Therefore, in the state in which the device main body is suspended, the fluid inlet of the first chamber can be positioned lower than the fluid outlet of the second chamber. Consequently, with a simple and economical configuration, it is possible to provide the biological component separation device which is capable of automatically performing the priming operation.

DESCRIPTION OF EMBODIMENTS

A preferred embodiment of a biological component separation device according to the present invention will be presented and described in detail below with reference to the accompanying drawings.

Figure 1:
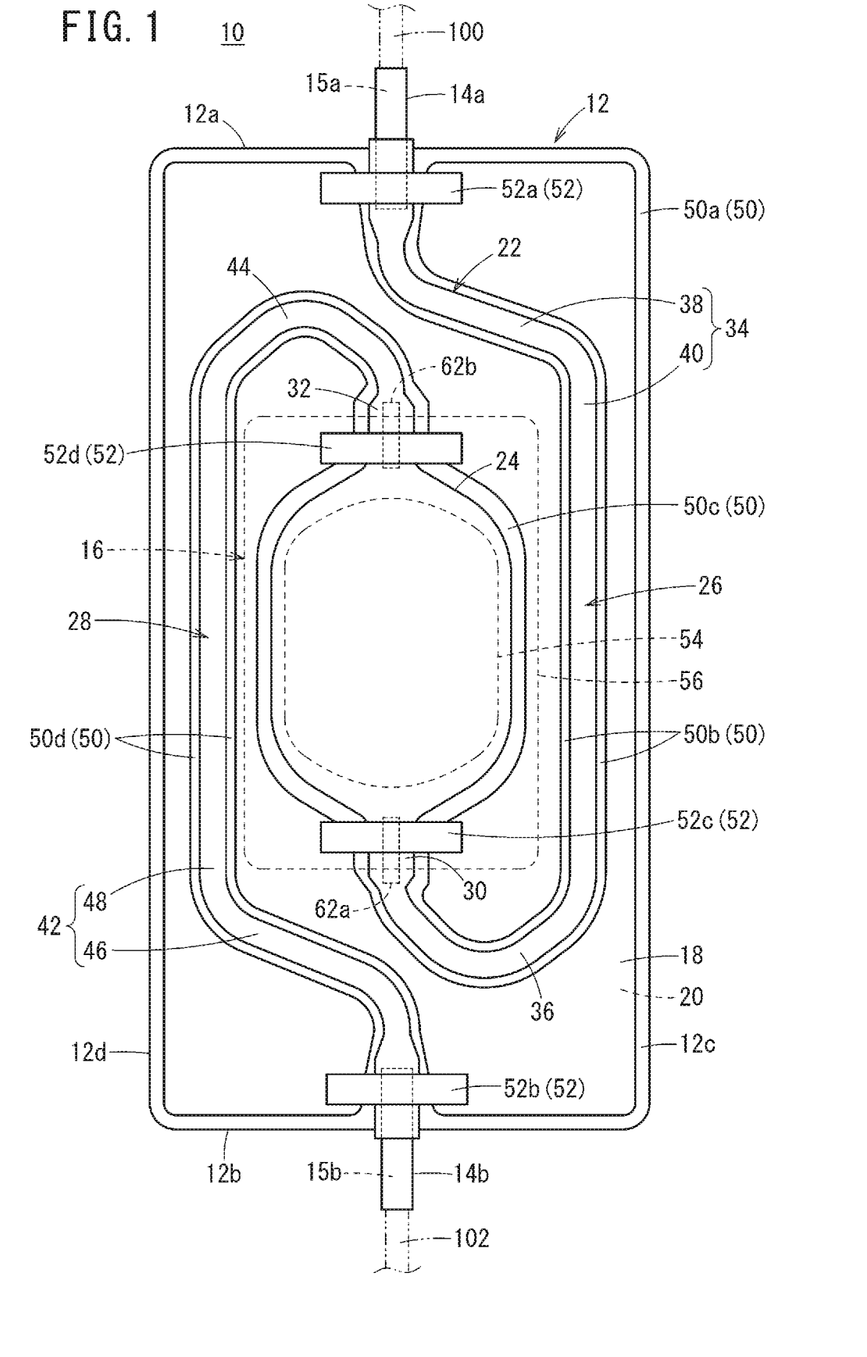
FIG. 1 is a plan view of a biological component separation device according to an embodiment of the present invention.

A biological component separation device 10 shown in FIG. 1 is in the form of a biological component separation cassette that is configured to separate a biological component from a biological fluid. More specifically, the biological component separation device 10 is configured in the form of, for example, a blood component separation device that separates a predetermined blood component (such as white blood cells or the like) from blood. However, the biological component separation device 10 may also be configured in the form of, for example, a cell component separation device that separates a predetermined cell component from cells.

The biological component separation device 10 is discarded after each single use in order to prevent contamination and promote hygiene. As shown in FIG. 1, the biological component separation device 10 includes a device main body 12, an introduction port member 14a (introduction port unit), a lead-out port member 14b (lead-out port unit), and a filter member 16.

The device main body 12 is formed in a rectangular shape as viewed in plan. The device main body 12 includes a first end portion 12a that is one end portion in a longitudinal direction, a second end portion 12b that is another end portion in the longitudinal direction, a first side portion 12c that is a side portion on one side in a lateral direction, and a second side portion 12d that is a side portion on another end side in the lateral direction.

The device main body 12 is formed of a soft material in a sheet-like shape. More specifically, the device main body 12 includes a first sheet 18 and a second sheet 20 formed of a soft material. The first sheet 18 and the second sheet 20 are joined together in a state of being superimposed on one another in a thickness direction. As examples of the means for joining the first sheet 18 and the second sheet 20, there may be cited fusion bonding (high frequency fusion bonding, thermal fusion bonding, etc.), adhesion, and the like.

As examples of the soft material that constitutes the first sheet 18 and the second sheet 20, there may be cited, for example, vinyl chloride, polyolefin, polyurethane, and the like. As examples of a vinyl chloride plasticizer, there may be cited diisononylcyclohexane-1,2-dicarboxylate, bis-2-ethylhexyl phthalate, and the like.

The introduction port member 14a and the lead-out port member 14b, which are made of a hard material (for example, vinyl chloride, polypropylene, polycarbonate, or the like), are provided on an outer peripheral edge of the device main body 12. The introduction port member 14a is disposed on the first end portion 12a of the device main body 12. The introduction port member 14a is positioned in the center of the device main body 12 in a widthwise direction. An introduction tube 100 is connected to the introduction port member 14a. The lead-out port member 14b is disposed on the second end portion 12b of the device main body 12. The lead-out port member 14b is positioned in the center of the device main body 12 in the widthwise direction. A lead-out tube 102 is connected to the lead-out port member 14b.

A flow path 22 through which the biological fluid flows is formed in the device main body 12. The flow path 22 is formed between the first sheet 18 and the second sheet 20. The flow path 22 includes a filter accommodating unit 24, an introduction line 26 (first line), and a lead-out line 28 (second line).

The filter accommodating unit 24 is positioned approximately in the center of the device main body 12 and accommodates the filter member 16. An internal space S of the filter accommodating unit 24 is partitioned by the filter member 16 into a first chamber 17a and a second chamber 17b in the thickness direction of the device main body 12 (see FIG. 2). The lead-out line 28 is connected to one end portion of the filter accommodating unit 24 in the longitudinal direction of the device main body 12. The introduction line 26 is connected to another end portion of the filter accommodating unit 24 in the longitudinal direction of the device main body 12. More specifically, a filter accommodating unit inlet 30 (fluid inlet) where the filter accommodating unit 24 and the introduction line 26 are connected is positioned more closely to a side (the side of the second end portion 12b) where the lead-out port member 14b is positioned than a filter accommodating unit outlet 32 (fluid outlet) where the filter accommodating unit 24 and the lead-out line 28 are connected.

Figure 2:
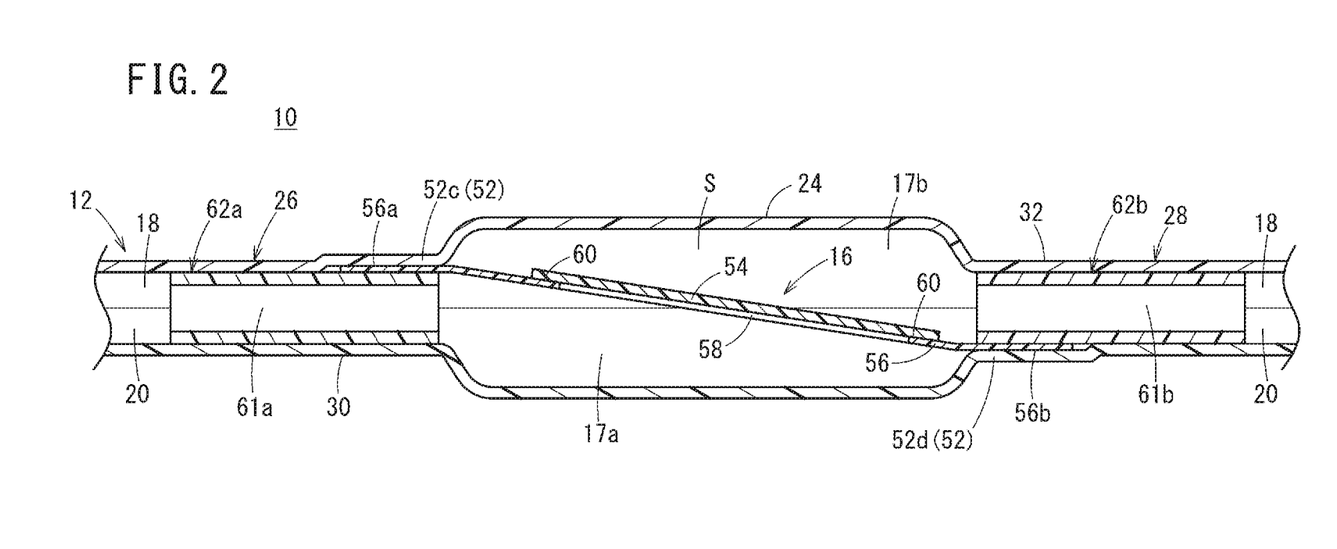
FIG. 2 is a longitudinal cross-sectional view of a filter accommodating unit and a filter member of a device main body shown in FIG. 1.

As shown in FIGS. 1 and 2, the introduction line 26 enables mutual communication between an interior hole 15a of the introduction port member 14a and the first chamber 17a of the filter accommodating unit 24. Stated otherwise, the introduction line 26 interconnects the introduction port member 14a and the first chamber 17a. More specifically, the introduction line 26 is a flow passage that guides the biological fluid from the introduction port member 14a into the first chamber 17a. One end portion of the introduction line 26 is connected to the introduction port member 14a, and another end portion of the introduction line 26 is connected to the other end portion (filter accommodating unit inlet 30) of the filter accommodating unit 24.

As shown in FIG. 1, the introduction line 26 includes an introduction extension portion 34 and an introduction turn portion 36. The introduction extension portion 34 extends from the introduction port member 14a toward a side (the side of the second end portion 12b) where the lead-out port member 14b is positioned, an extending end of the introduction extension portion 34 being positioned more closely to the side where the lead-out port member 14b is positioned than the filter accommodating unit 24. The introduction extension portion 34 includes a first inclined section 38, which extends from the introduction port member 14a toward the first side portion 12c and is inclined toward the side of the second end portion 12b, and a first straight section 40, which extends from an extending end of the first inclined section 38 toward the side where the lead-out port member 14b is positioned, an extending end of the first straight section 40 being positioned more closely to the side where the lead-out port member 14b is positioned than the filter accommodating unit 24.

The first straight section 40 extends along the longitudinal direction of the device main body 12. The first straight section 40 is positioned on one side (the side of the first side portion 12c) in a lateral direction of the device main body 12 with respect to the filter accommodating unit 24. Stated otherwise, the first straight section 40 is positioned between the filter accommodating unit 24 and the first side portion 12c. The extending end of the first straight section 40 is positioned more closely to the side of the second end portion 12b than the filter accommodating unit 24.

The introduction turn portion 36 curves from the extending end of the introduction extension portion 34 toward the side where the filter accommodating unit 24 is positioned, and extends to the filter accommodating unit inlet 30. The introduction turn portion 36 is curved 180°. Stated otherwise, as viewed in plan, the introduction turn portion 36 is formed in a U-shape.

As shown in FIGS. 1 and 2, the lead-out line 28 enables mutual communication between an interior hole 15b of the lead-out port member 14b and the second chamber 17b of the filter accommodating unit 24. Stated otherwise, the lead-out line 28 interconnects the lead-out port member 14b and the second chamber 17b. More specifically, the lead-out line 28 is a flow passage that guides the biological fluid in the interior of the second chamber 17b into the lead-out port member 14b. One end portion of the lead-out line 28 is connected to one end portion (the filter accommodating unit outlet 32) of the filter accommodating unit 24, and another end portion of the lead-out line 28 is connected to the lead-out port member 14b.

As shown in FIG. 1, the lead-out line 28 includes a lead-out extension portion 42 and a lead-out turn portion 44. The lead-out extension portion 42 extends from the lead-out port member 14b toward a side (the side of the first end portion 12a) where the introduction port member 14a is positioned, an extending end of the lead-out extension portion 42 being positioned more closely to the side where the introduction port member 14a is positioned than the filter accommodating unit 24. The lead-out extension portion 42 includes a second inclined section 46, which extends from the lead-out port member 14b toward the second side portion 12d and is inclined toward the side of the first end portion 12a, and a second straight section 48, which extends from an extending end of the second inclined section 46 toward the side where the introduction port member 14a is positioned, an extending end of the second straight section 48 being positioned more closely to the side where the introduction port member 14a is positioned than the filter accommodating unit 24.

The second straight section 48 extends along the longitudinal direction of the device main body 12. The second straight section 48 is positioned on another side (the side of the second side portion 12d) in the lateral direction of the device main body 12 with respect to the filter accommodating unit 24. Stated otherwise, the second straight section 48 is positioned between the filter accommodating unit 24 and the second side portion 12d. The extending end of the second straight section 48 is positioned more closely to the side of the first end portion 12a than the filter accommodating unit 24.

The lead-out turn portion 44 curves from the extending end of the lead-out extension portion 42 toward the side where the filter accommodating unit 24 is positioned, and extends to the filter accommodating unit outlet 32. The lead-out turn portion 44 is curved 180°. Stated otherwise, as viewed in plan, the lead-out turn portion 44 is formed in a U-shape.

The filter accommodating unit inlet 30 and the filter accommodating unit outlet 32 are positioned in the center of the filter accommodating unit 24 in the lateral direction of the device main body 12. Stated otherwise, the filter accommodating unit inlet 30 and the filter accommodating unit outlet 32 are positioned in the center of the device main body 12 in the lateral direction.

The filter accommodating unit 24 is sandwiched between the first straight section 40 and the second straight section 48 in the lateral direction of the device main body 12. The introduction port member 14a, the filter accommodating unit inlet 30, the filter accommodating unit outlet 32, and the lead-out port member 14b are arranged on the same straight line along the longitudinal direction of the device main body 12. Incidentally, although the introduction port member 14a, the filter accommodating unit inlet 30, the filter accommodating unit outlet 32, and the lead-out port member 14b are preferably positioned in the center of the device main body 12 in the lateral direction, they are not particularly limited to such an arrangement, and they need not necessarily be arranged on the same straight line. When the introduction port member 14a and the lead-out port member 14b are positioned in the center of the device main body 12 in the lateral direction, it is possible to suppress a situation in which the biological component separation device 10 becomes tilted (the longitudinal direction of the device main body 12 becomes inclined with respect to the vertical direction) when the biological component separation device 10 is suspended.

Sealed portions 50, which are fusion-bonded locations between the first sheet 18 and the second sheet 20, are formed in the device main body 12. The sealed portions 50 include an outer edge sealed portion 50a, a first sealed portion 50b, a second sealed portion 50c, and a third sealed portion 50d. The outer edge sealed portion 50a is formed along the outer peripheral edge of the device main body 12. The first sealed portion 50b is formed over the entire length on both sides of the introduction line 26. The second sealed portion 50c is formed along the outer periphery of the filter accommodating unit 24. The third sealed portion 50d is formed over the entire length on both sides of the lead-out line 28.

Further, fixing members 52 are formed in the device main body 12. The fixing members 52 include a first fixing member 52a, a second fixing member 52b, a third fixing member 52c, and a fourth fixing member 52d. The first fixing member 52a fixes the introduction port member 14a to the device main body 12. The first fixing member 52a extends along the lateral direction of the device main body 12 so as to cross over the introduction port member 14a. The first sheet 18 and the second sheet 20 are fixed (sealed) to each other at both ends of the first fixing member 52a. In a central part of the first fixing member 52a, the first sheet 18 and the introduction port member 14a are fixed (sealed) to each other, and the second sheet 20 and the introduction port member 14a are fixed (sealed) to each other.

The second fixing member 52b fixes the lead-out port member 14b to the device main body 12. The second fixing member 52b extends along the lateral direction of the device main body 12 so as to cross over the lead-out port member 14b. The first sheet 18 and the second sheet 20 are fixed (sealed) to each other at both ends of the second fixing member 52b. In a central part of the second fixing member 52b, the first sheet 18 and the lead-out port member 14b are fixed (sealed) to each other, and the second sheet 20 and the lead-out port member 14b are fixed (sealed) to each other.

The third fixing member 52c fixes the filter member 16 and a later-described first tube 62a to the filter accommodating unit 24. The fourth fixing member 52d fixes the filter member 16 and a later-described second tube 62b to the filter accommodating unit 24. Detailed descriptions of the third fixing member 52c and the fourth fixing member 52d will be discussed later.

In the device main body 12, locations other than the sealed portions 50 and the fixing members 52 are non-sealed portions where the first sheet 18 and the second sheet 20 are not joined (fusion bonded) to each other. Since the sealed portions 50 are applied with pressure during formation thereof, the sealed portions 50 are smaller in thickness than the non-sealed portions, and are recessed with respect to the non-sealed portions. Stated otherwise, the non-sealed portions protrude in the thickness direction with respect to the sealed portions 50. The wall portions that form the flow path 22 within the device main body 12 bulge in convex shapes in the thickness direction of the device main body 12 on both side surfaces of the device main body 12. Accordingly, the flow path 22 is opened in its natural state.

As shown in FIG. 2, the filter member 16 is disposed so as to partition the internal space S of the filter accommodating unit 24 into the first chamber 17a and the second chamber 17b in the thickness direction of the device main body 12. The filter member 16 includes a filter main body 54 and a support sheet 56 that supports the filter main body 54.

The filter main body 54 serves as a filter medium that separates (removes and traps) a predetermined biological component from the biological fluid. The filter main body 54 is made of a sheet-like porous body having fine communication holes that communicate from one surface to the other surface thereof. As examples of such a porous body, there may be cited a polyurethane sponge sheet and a non-woven fabric. Although a detailed illustration thereof is omitted, the filter main body 54 is formed by laminating a plurality of (for example, on the order of two to ten) layers. However, the filter main body 54 may also be constituted by a single layer.

The support sheet 56 is formed of a resin material so that liquid is incapable of passing therethrough. As shown in FIG. 1, the outer shape of the support sheet 56 is formed in a rectangular shape. The longitudinal direction of the support sheet 56 lies along the longitudinal direction of the device main body 12. The support sheet 56 extends in an encircling manner around the outside of the filter main body 54.

As shown in FIG. 2, a hole 58 that is covered by the filter main body 54 is formed in a central part of the support sheet 56. The hole 58 extends in the direction in which the support sheet 56 extends. On an outer peripheral side of the hole 58 within the support sheet 56, a filter seal member 60, which prevents the biological fluid from flowing between the filter main body 54 and the support sheet 56, is provided. The filter seal member 60 joins the filter main body 54 to the support sheet 56 in a liquid-tight manner. The filter seal member 60 extends around an outer peripheral edge of the filter main body 54. An outer peripheral edge of the support sheet 56 is joined (fusion bonded) in a liquid-tight manner to the first sheet 18 and the second sheet 20 by the second sealed portion 50c (see FIG. 1).

As shown in FIG. 2, the first tube 62a which includes an interior hole 61a communicating with the first chamber 17a is disposed inside an end portion of the introduction line 26 on the side of the filter accommodating unit 24. The first tube 62a extends along the longitudinal direction of the device main body 12 (see FIG. 1). A first region 56a of the support sheet 56 is sandwiched between the first tube 62a and the first sheet 18.

As shown in FIGS. 1 and 2, the first tube 62a and the first region 56a of the support sheet 56 are fixed to the device main body 12 by the third fixing member 52c. The third fixing member 52c extends along the lateral direction of the device main body 12 so as to cross over the first tube 62a. The first sheet 18 and the second sheet 20 are fixed (sealed) to each other at both ends of the third fixing member 52c. In a central part of the third fixing member 52c, the first sheet 18 and the first region 56a of the support sheet 56 are fixed (sealed) to each other, the first region 56a of the support sheet 56 and the first tube 62a are fixed (sealed) to each other, and further, the second sheet 20 and the first tube 62a are fixed (sealed) to each other.

As shown in FIG. 2, the second tube 62b which includes an interior hole 61b communicating with the second chamber 17b is disposed inside an end portion of the lead-out line 28 on the side of the filter accommodating unit 24. The first tube 62a and the second tube 62b are arranged so as to face each other with the internal space S interposed therebetween. The second tube 62b extends along the longitudinal direction of the device main body 12. A second region 56b of the support sheet 56 is sandwiched between the second tube 62b and the second sheet 20.

As shown in FIGS. 1 and 2, the second tube 62b and the second region 56b of the support sheet 56 are fixed to the device main body 12 by the fourth fixing member 52d. The fourth fixing member 52d extends along the lateral direction of the device main body 12 so as to cross over the second tube 62b. The first sheet 18 and the second sheet 20 are fixed (sealed) to each other at both ends of the fourth fixing member 52d. In a central part of the fourth fixing member 52d, the second sheet 20 and the second region 56b of the support sheet 56 are fixed (sealed) to each other, the second region 56b of the support sheet 56 and the second tube 62b are fixed (sealed) to each other, and further, the first sheet 18 and the second tube 62b are fixed (sealed) to each other.

Figure 3A:
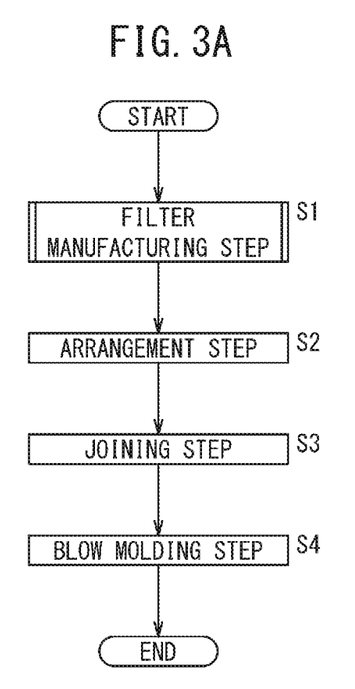
FIG. 3A is a flowchart illustrating a manufacturing method of the biological component separation device of FIG. 1.

The above-described biological component separation device 10 can be manufactured, for example, by the following manufacturing method. As shown in FIG. 3A, a method of manufacturing the biological component separation device 10 according to the present embodiment includes a filter manufacturing step (step S1), an arrangement step (step S2), a joining step (step S3), and a blow molding step (step S4).

Figure 3B:
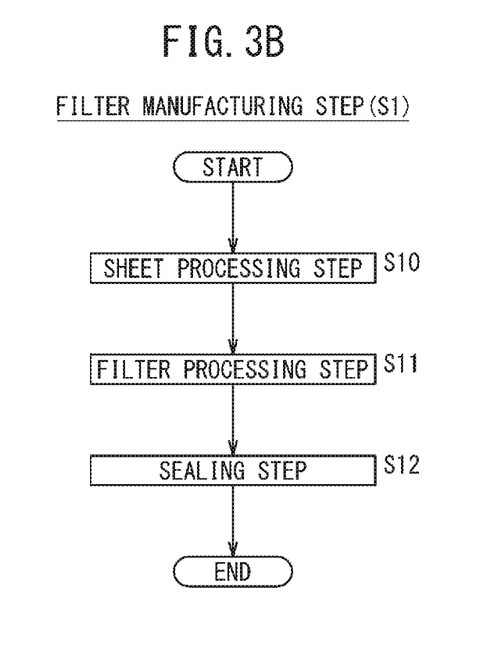
FIG. 3B is a flowchart illustrating a filter manufacturing step.
Figure 4A:
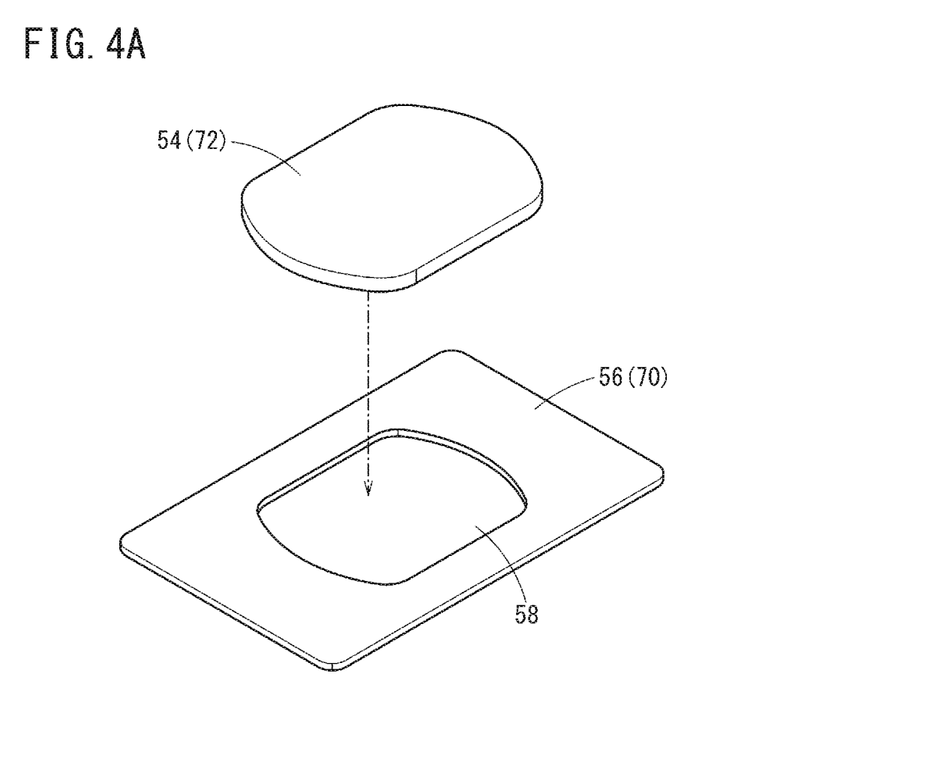
FIG. 4A is a first explanatory diagram of the filter manufacturing step.

As shown in FIG. 3B, the filter manufacturing step (step S1 of FIG. 3A) includes a sheet processing step (step S10), a filter processing step (step S11), and a sealing step (step S12). In the sheet processing step (step S10 of FIG. 3B), as shown in FIG. 4A, a sheet material 70 is punched into a rectangular shape and the hole 58 is punched in a central part of the rectangle, whereby the support sheet 56 is formed. Moreover, in the sheet processing step, the sheet material 70 may be cut out into the shape of the support sheet 56 using a laser processing apparatus or the like. In the filter processing step (step S11), the filter main body 54 is formed by punching a sheet-like filter material 72. The filter main body 54 is formed to be slightly larger than the hole 58 of the support sheet 56.

Figure 4B:
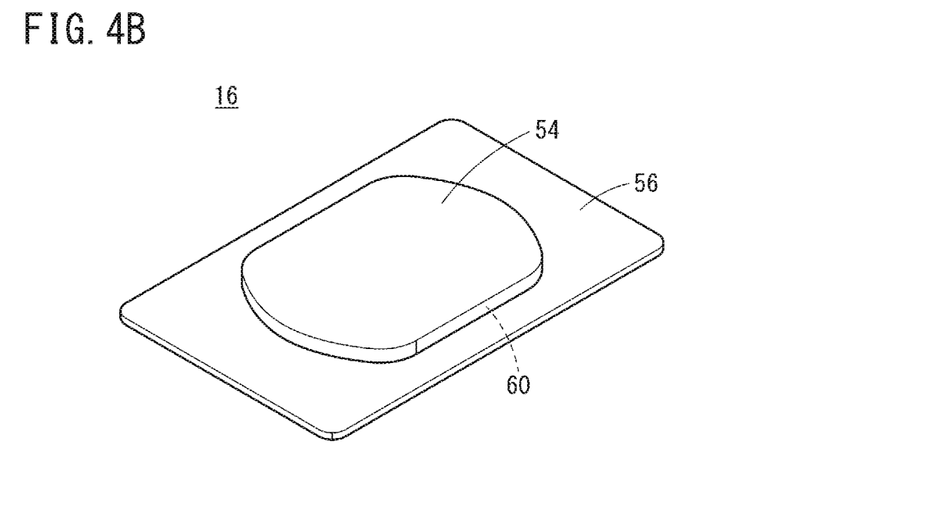
FIG. 4B is a second explanatory diagram of the filter manufacturing step.

In the sealing step (step S12), as shown in FIG. 4B, the filter seal member 60 is formed by peripherally joining the outer peripheral edge of the filter main body 54 to the support sheet 56, in a state where the filter main body 54 is superimposed on one surface of the support sheet 56 so as to cover the hole 58 of the support sheet 56. By carrying out the foregoing steps, the filter member 16 is manufactured.

Figure 5:
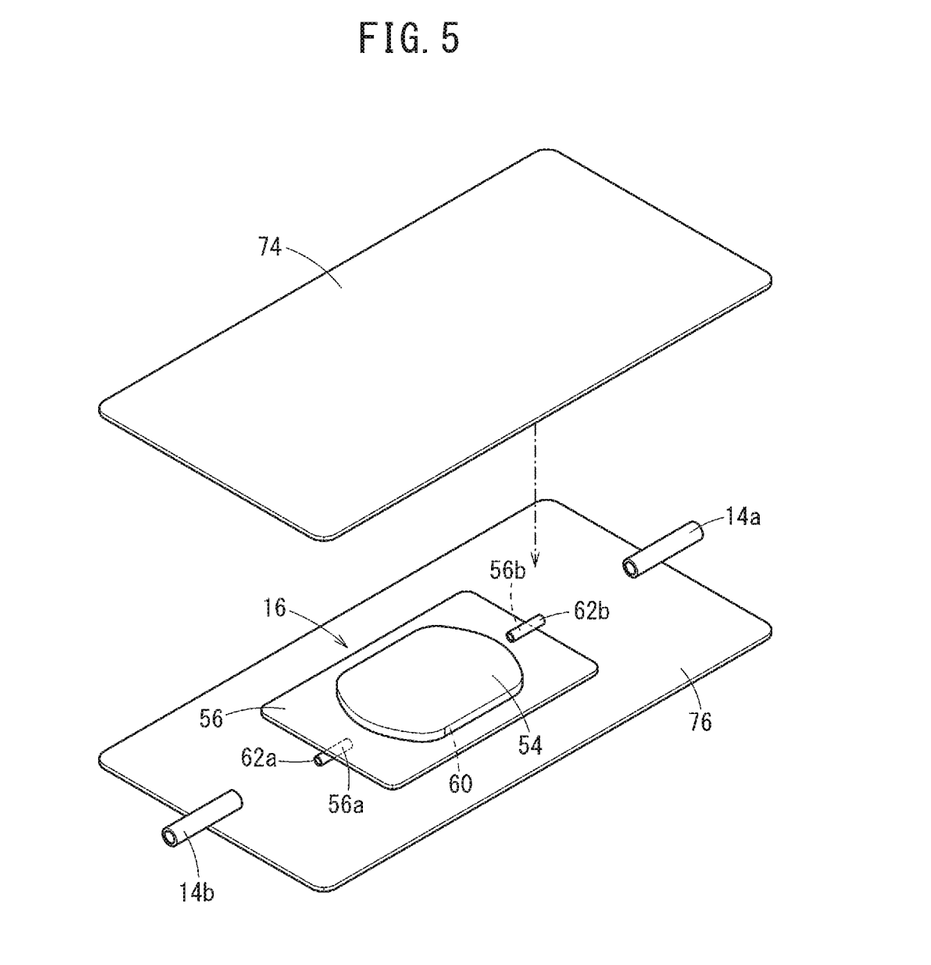
FIG. 5 is an explanatory diagram of an arrangement step.

Subsequently, in the arrangement step (step S2 of FIG. 3A), as shown in FIG. 5, the introduction port member 14a, the lead-out port member 14b, the filter member 16, the first tube 62a, and the second tube 62b are set so as to be arranged between a first material sheet 74 which is formed of a soft material, and a second material sheet 76 which is formed of a soft material.

The introduction port member 14a is arranged between one end portion of the first material sheet 74 and one end portion of the second material sheet 76. The lead-out port member 14b is arranged between another end portion of the first material sheet 74 and another end portion of the second material sheet 76. The filter member 16 is arranged between a central part of the first material sheet 74 and a central part of the second material sheet 76. The first region 56a of the support sheet 56 is arranged between the first tube 62a and the first material sheet 74, and the second region 56b of the support sheet 56 is arranged between the second tube 62b and the second material sheet 76.

Figure 6A:
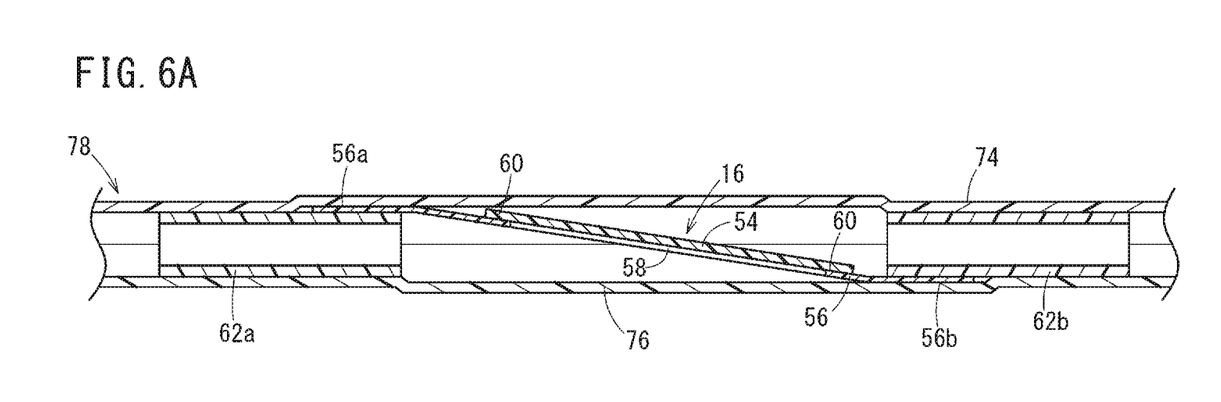
FIG. 6A is an explanatory diagram of a joining step.

In the joining step (step S3 of FIG. 3A), the introduction port member 14a is joined to the first sheet 18 and the second sheet 20, and the lead-out port member 14b is joined to the first sheet 18 and the second sheet 20. Further, as shown in FIG. 6A, the first region 56a is joined to the first sheet 18 and the first tube 62a, and the second region 56b is joined to the second sheet 20 and the second tube 62b. In this case, during such joining, a high-frequency fusion bonding device, or a thermal fusion bonding device or the like is used.

Figure 6B:
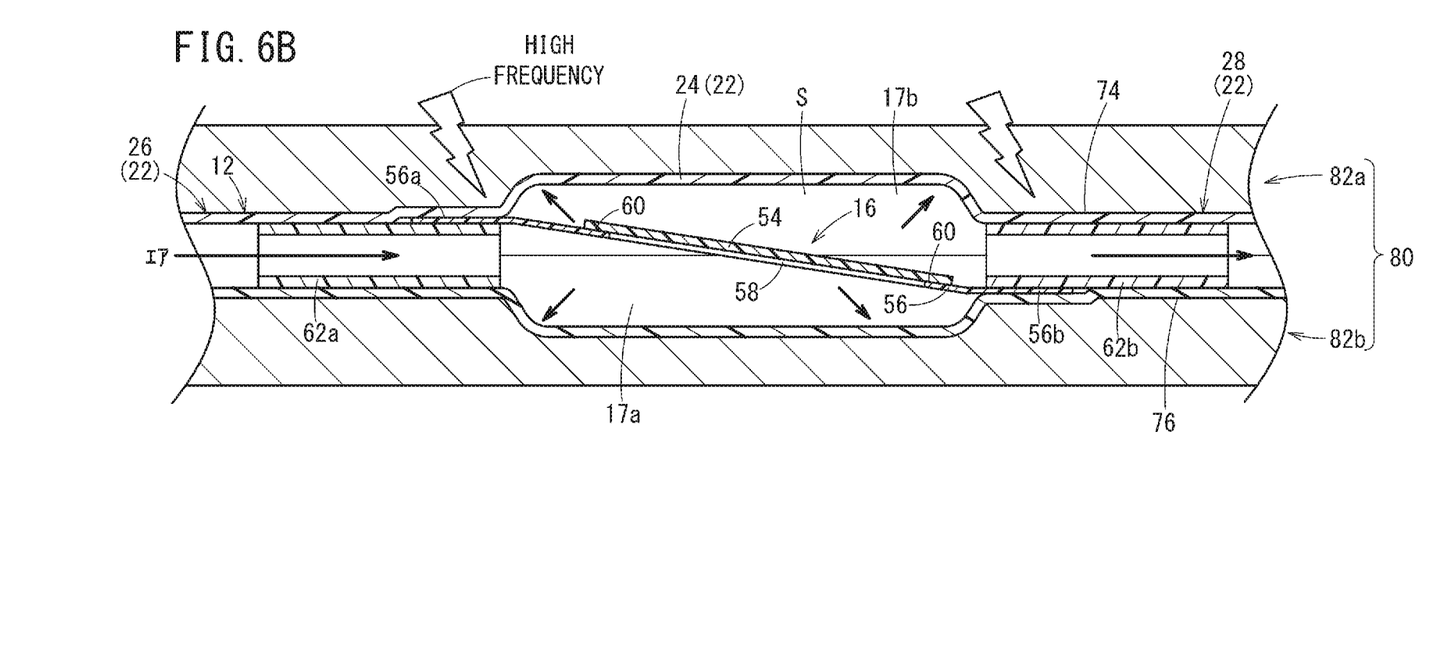
FIG. 6B is an explanatory diagram of a blow molding step.

An intermediate product 78 which is obtained in the joining step is disposed at a predetermined position between a pair of molds 82a and 82b that make up a sheet joining device 80 shown in FIG. 6B. In the present embodiment, the sheet joining device 80 is a high frequency fusion bonding device. The sheet joining device 80 may also be a thermal fusion bonding device or the like. On molding surfaces of the pair of molds 82a and 82b, grooves are provided for the purpose of forming portions (convex wall portions) that surround the flow path 22 of the device main body 12.

In the blow molding step (step S4 of FIG. 3A), as shown in FIG. 6B, the first material sheet 74 and the second material sheet 76 are sandwiched between the molds 82a and 82b, and the first material sheet 74 and the second material sheet 76 are joined, together with blow molding being performed so as to form the flow path 22 in which the filter member 16 is arranged.

More specifically, the pair of molds 82a and 82b are closed, the first material sheet 74 and the second material sheet 76 are overlapped, and predetermined locations of the first material sheet 74 and the second material sheet 76 are subjected to high frequency fusion bonding so as to form the flow path 22 (the filter accommodating unit 24, the introduction line 26, and the lead-out line 28). At this time, air is blown out from a non-illustrated blow nozzle, and in the first material sheet 74 and the second material sheet 76, locations thereof corresponding to the grooves provided in the molds 82a and 82b are inflated, whereby the flow path 22 (the filter accommodating unit 24, the introduction line 26, and the lead-out line 28) are formed.

Since the air blown out from the blow nozzle passes through the filter main body 54, the air is reliably supplied to the back side of the filter member 16. Consequently, the device main body 12 is molded, which includes the first sheet 18 and the second sheet 20 that are joined to each other, and in which the flow path 22 is formed and the filter member 16 is incorporated. After completion of the blow molding step, the blow nozzle is pulled out from the device main body 12. Next, the pair of molds 82a and 82b are opened, and the device main body 12, which is a molded product, is taken out.

Figure 7:
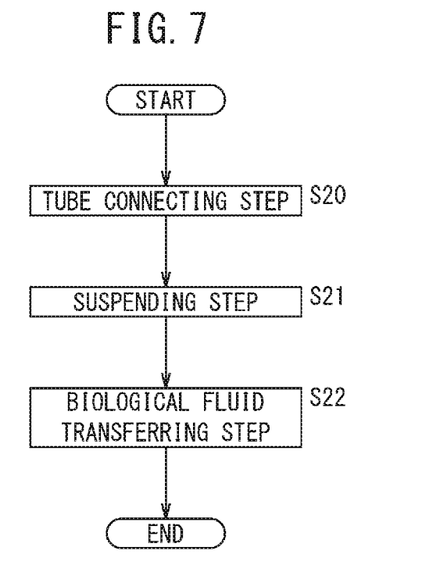
FIG. 7 is a flowchart illustrating a biological component separation method in which the biological component separation device of FIG. 1 is utilized.

Next, a description will be given of a biological component separation method (blood component separation method) in which the biological component separation device 10 according to the present embodiment is utilized. As shown in FIG. 7, the biological component separation method includes a tube connecting step (step S20), a suspending step (step S21), and a biological fluid transferring step (step S22).

Figure 8:
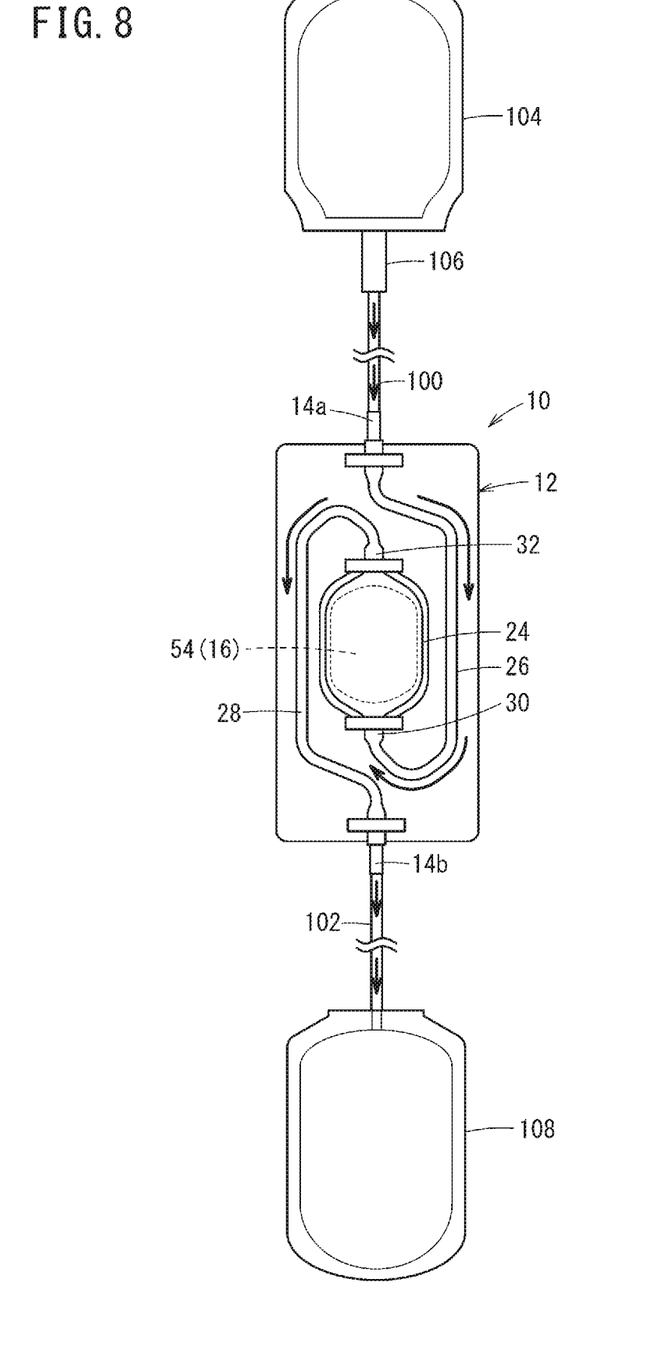
FIG. 8 is an explanatory diagram of the biological component separation method.

In the tube connecting step (step S20 of FIG. 7), as shown in FIG. 8, the introduction tube 100 is connected to the introduction port member 14a, and the lead-out tube 102 is connected to the lead-out port member 14b. One end portion of the introduction tube 100 is connected to a sealing member 106 of a biological fluid bag 104, and another end portion of the introduction tube 100 is connected to the introduction port member 14a. A biological fluid (for example, blood or cells) is accommodated in the biological fluid bag 104. One end portion of the lead-out tube 102 is connected to the lead-out port member 14b, and another end portion of the lead-out tube 102 is connected to an accommodating bag 108.

In the suspending step (step S21 of FIG. 7), the biological fluid bag is suspended from a non-illustrated suspension platform. At this time, the device main body 12 is suspended by the introduction tube 100. More specifically, the device main body 12 is suspended by the introduction tube 100 so that the longitudinal direction thereof lies along the vertical direction.

In this state, the filter accommodating unit inlet 30 connecting the filter accommodating unit 24 and the introduction line 26 is positioned lower than the filter accommodating unit outlet 32 connecting the filter accommodating unit 24 and the lead-out line 28. Stated otherwise, in the state in which the device main body 12 is suspended, the filter accommodating unit inlet 30 is positioned at a lower end of the filter accommodating unit 24, and the filter accommodating unit outlet 32 is positioned at an upper end of the filter accommodating unit 24. Further, the introduction port member 14a, the filter accommodating unit inlet 30, the filter accommodating unit outlet 32, and the lead-out port member 14b are arranged on the same straight line along the vertical direction. In the state in which the device main body 12 is suspended, the filter member 16 extends along the vertical direction.

In the biological fluid transferring step (step S22 of FIG. 7), the sealing member 106 of the biological fluid bag 104 is broken. Upon doing so, due to the difference in elevation (gravity), the biological fluid in the biological fluid bag 104 passes through the introduction tube 100, the introduction port member 14a, and the introduction line 26, and flows into the first chamber 17a from the filter accommodating unit inlet 30 which is positioned at the lower end of the filter accommodating unit 24.

While air that exists within the internal space S of the filter accommodating unit 24 is discharged into the lead-out line 28 from the filter accommodating unit outlet 32 that is positioned at the upper end of the filter accommodating unit 24, the biological fluid that has flowed into the first chamber 17a spreads throughout the first chamber 17a of the filter accommodating unit 24 and flows through the filter main body 54 into the second chamber 17b. Then, by the internal space S (the first chamber 17a and the second chamber 17b) of the filter accommodating unit 24 being filled with the biological fluid, the filter accommodating unit 24 is automatically primed.

When the biological fluid inside the first chamber 17a flows through the filter main body 54, a predetermined biological component (for example, a blood component such as white blood cells or a cell component) from the biological fluid becomes trapped in the filter main body 54. Stated otherwise, the biological component is separated (removed) from the biological fluid. At this time, since almost no air exists in the internal space S of the filter accommodating unit 24, separation of the biological component by the filter main body 54 is carried out efficiently.

The biological fluid that has flowed through the filter main body 54 (the biological fluid after the biological component has been separated therefrom) flows through the filter accommodating unit outlet 32, the lead-out line 28, the lead-out port member 14b, and the lead-out tube 102, and is accommodated inside the accommodating bag 108.

In this case, the biological component separation device 10 according to the present embodiment exhibits the following effects.

In the biological component separation device 10, in a state in which the device main body 12 is suspended by the introduction tube 100, the filter accommodating unit inlet 30 where the filter accommodating unit 24 and the introduction line 26 are connected is positioned lower than the filter accommodating unit outlet 32 where the filter accommodating unit 24 and the lead-out line 28 are connected.

In accordance with such a configuration, in the state in which the device main body 12 is suspended, since the filter accommodating unit inlet 30 is positioned lower than the filter accommodating unit outlet 32, the priming operation can be performed automatically without turning the device main body 12 upside down. More specifically, in the state in which the device main body 12 is suspended, by the biological fluid that is introduced from the introduction line 26 into the filter accommodating unit 24 via the filter accommodating unit inlet 30 that is positioned downwardly, it is possible for the air inside the filter accommodating unit 24 to be discharged into the lead-out line 28 via the upwardly positioned filter accommodating unit outlet 32. Further, since the introduction line 26 and the lead-out line 28 are provided in the device main body 12 which is formed in a sheet-like shape, the biological component separation device 10 can be manufactured at a lower cost in comparison with a case in which the introduction line 26, the lead-out line 28, and the device main body 12 are molded separately. Accordingly, it is possible for the biological component separation device 10 to be constituted in a simple and economical manner.

In the state in which the device main body 12 is suspended, the filter accommodating unit inlet 30 is positioned at the lower end of the filter accommodating unit 24. In accordance with such a configuration, the air inside the filter accommodating unit 24 can be efficiently discharged into the lead-out line 28.

In the state in which the device main body 12 is suspended, the filter accommodating unit outlet 32 is positioned at the upper end of the filter accommodating unit 24. In accordance with such a configuration, the air inside the filter accommodating unit 24 can be more efficiently discharged into the lead-out line 28.

The device main body 12 extends in one direction, the introduction port member 14a is disposed at one end portion of the device main body 12, the lead-out port member 14b is disposed at another end portion of the device main body 12, and the filter accommodating unit inlet 30 is positioned more closely to a side where the lead-out port member 14b is positioned than the filter accommodating unit outlet 32. In accordance with such a configuration, in the state in which the device main body 12 is suspended, the filter accommodating unit inlet 30 can be positioned lower than the filter accommodating unit outlet 32 with a simple configuration.

The introduction port member 14a, the filter accommodating unit inlet 30, the filter accommodating unit outlet 32, and the lead-out port member 14b are arranged on the same straight line along the longitudinal direction of the device main body 12. In accordance with such a configuration, the device main body 12 can be suspended in a well balanced manner by the introduction tube 100.

The introduction line 26 is positioned on one side of the device main body 12 in a lateral direction with respect to the filter accommodating unit 24, and the lead-out line 28 is positioned on another side of the device main body 12 in the lateral direction with respect to the filter accommodating unit 24. In accordance with such a configuration, the device main body 12 can be suspended in a well balanced manner by the introduction tube 100.

The introduction line 26 includes the introduction extension portion 34 that extends from the introduction port member 14a toward the side where the lead-out port member 14b is positioned, the extending end of the introduction extension portion 34 being positioned more closely to the side where the lead-out port member 14b is positioned than the filter accommodating unit 24, and the introduction turn portion 36 which curves from the extending end of the introduction extension portion 34 toward the side where the filter accommodating unit 24 is positioned, and extends to the filter accommodating unit inlet 30. The lead-out line 28 includes the lead-out extension portion 42 that extends from the lead-out port member 14b toward the side where the introduction port member 14a is positioned, the extending end of the lead-out extension portion 42 being positioned more closely to the side where the introduction port member 14a is positioned than the filter accommodating unit 24, and the lead-out turn portion 44 which curves from the extending end of the lead-out extension portion 42 toward the side where the filter accommodating unit 24 is positioned, and extends to the filter accommodating unit outlet 32.

In accordance with such a configuration, the device main body 12 can be suspended in a well balanced manner by the introduction tube 100 with a simple configuration.

The device main body 12 is formed by mutually joining together in a state of being superimposed on one another in the thickness direction, the first sheet 18 and the second sheet 20 being made of a soft material, and the filter accommodating unit 24, the introduction line 26, and the lead-out line 28 are formed between the first sheet 18 and the second sheet 20. In accordance with such a configuration, it is possible to easily manufacture the biological component separation device 10.

The filter member 16 includes the filter main body 54, and the support sheet 56 joined in a liquid-tight manner to the outer edge portion of the filter main body 54 so as to encircle the filter main body 54, and the outer edge portion of the support sheet 56 is joined in a liquid-tight manner to the device main body 12. In accordance with such a configuration, the filter member 16 can be easily manufactured.

The biological component separation device 10 comprises the device main body 12 formed of a soft material in a sheet-like shape, the filter member 16 that partitions the internal space S of the filter accommodating unit 24, which is provided in the device main body 12 and is equipped with the fluid inlet (filter accommodating unit inlet 30) and the fluid outlet (filter accommodating unit outlet 32), into the first chamber 17a and the second chamber 17b, and that captures the predetermined biological component, the introduction port unit (introduction port member 14a) that is disposed in the device main body 12 and introduces the biological fluid, the lead-out port unit (lead-out port member 14b) that is disposed in the device main body 12 and delivers out the biological fluid, the first line (introduction line 26) connecting the fluid inlet (filter accommodating unit inlet 30) provided in the first chamber 17a and the introduction port unit (introduction port member 14a), and the second line (lead-out line 28) connecting the fluid outlet (filter accommodating unit outlet 32) provided in the second chamber 17b and the lead-out port unit (lead-out port member 14b). The fluid inlet (filter accommodating unit inlet 30) of the first chamber 17a and the lead-out port unit (lead-out port member 14b) are positioned so as to face each other, and the fluid outlet (filter accommodating unit outlet 32) of the second chamber 17b and the introduction port unit (introduction port member 14a) are positioned so as to face each other.

In accordance with such a configuration, in the state in which the device main body 12 is suspended, the fluid inlet (filter accommodating unit inlet 30) of the first chamber 17a can be positioned lower than the fluid outlet (filter accommodating unit outlet 32) of the second chamber 17b. Consequently, with a simple and economical configuration, it is possible to provide the biological component separation device 10 which is capable of automatically performing the priming operation.

The present invention is not limited to the above-described configuration. The lead-out port member 14b may be provided on the first side portion 12c or the second side portion 12d. The shapes of the introduction line 26 and the lead-out line 28 can be arbitrarily changed. The filter accommodating unit inlet 30 and the filter accommodating unit outlet 32 may be arranged in any manner, insofar as the filter accommodating unit inlet 30 is positioned lower than the filter accommodating unit outlet 32 in the state in which the device main body 12 is suspended.

The biological component separation device according to the present invention is not limited to the above-described embodiment, and it goes without saying that various modifications could be adopted therein within a range that does not depart from the essence and gist of the present invention.

The invention claimed is:

1. A biological component separation device that separates a predetermined biological component from a biological fluid, the biological component separation device comprising:
   a device main body formed of a soft material in a sheet-like shape;
   a filter housing in the device main body, said filter housing having an internal space;
   a filter member configured to partition said internal space into a first chamber and a second chamber, and to capture the predetermined biological component;
   an introduction port member disposed in the device main body and configured to introduce the biological fluid; and
   a lead-out port member disposed in the device main body and configured to deliver out the biological fluid,
   wherein:
      the device main body is provided with an introduction line interconnecting the first chamber and the introduction port member, and a lead-out line interconnecting the second chamber and the lead-out port member;
      in a state in which the device main body is suspended, a filter housing inlet where the filter housing and the introduction line are connected is positioned lower than a filter housing outlet where the filter housing and the lead-out line are connected;
      the introduction line is positioned on the device main body along a first side of the filter housing; and
      the lead-out line is positioned on the device main body along a second side of the filter housing opposite the first side,
   wherein the introduction line comprises:
      an introduction extension portion extending from the introduction port member toward the lead-out port member, an extending end of the introduction extension portion being positioned closer to the lead-out port member than the filter housing; and
      an introduction turn portion which curves from the extending end of the introduction extension portion and extends to the filter housing inlet, and
   wherein the lead-out line comprises:
      a lead-out extension portion extending from the lead-out port member toward the introduction port member, an extending end of the lead-out extension portion being positioned closer to the introduction port member than the filter housing; and
      a lead-out turn portion which curves from the extending end of the lead-out extension portion and extends to the filter housing outlet.

2. The biological component separation device according to claim 1, wherein in the state in which the device main body is suspended, the filter housing inlet is positioned at a lower end of the filter housing.

3. The biological component separation device according to claim 2, wherein in the state in which the device main body is suspended, the filter housing outlet is positioned at an upper end of the filter housing.

4. The biological component separation device according to claim 1, wherein:
   the device main body extends in one direction;
   the introduction port member is disposed at one end portion of the device main body;
   the lead-out port member is disposed at another end portion of the device main body; and
   the filter housing inlet is positioned closer to the lead-out port member than the filter housing outlet.

5. The biological component separation device according to claim 1, wherein the introduction port member, the filter housing inlet, the filter housing outlet, and the lead-out port member are arranged on a same straight line along a longitudinal direction of the device main body.

6. The biological component separation device according to claim 1, wherein the introduction line and the lead-out line extend in a longitudinal direction of the device main body.

7. The biological component separation device according to claim 1, wherein:
   the device main body is formed by mutually joining together a first sheet and a second sheet in a state of being superimposed on one another in a thickness direction, the first sheet and the second sheet being made of the soft material; and
   the filter housing, the introduction line, and the lead-out line are formed between the first sheet and the second sheet.

8. The biological component separation device according to claim 1, wherein the filter member comprises:
a filter main body; and
a support sheet joined in a liquid-tight manner to an outer edge portion of the filter main body so as to encircle the filter main body, and
wherein an outer edge portion of the support sheet is joined in a liquid-tight manner to the device main body.

9. A biological component separation device that separates a predetermined biological component from a biological fluid, the biological component separation device comprising:
a device main body formed of a soft material in a sheet-like shape;
a filter housing in the device main body forming an internal space having a fluid inlet and a fluid outlet;
a filter member configured to partition said internal space into a first chamber and a second chamber, and to capture the predetermined biological component;
an introduction port disposed in the device main body and configured to introduce the biological fluid;
a lead-out port disposed in the device main body and configured to deliver out the biological fluid;
a first line connecting the fluid inlet provided in the first chamber and the introduction port; and
a second line connecting the fluid outlet provided in the second chamber and the lead-out port,
wherein:
the fluid inlet of the first chamber and the lead-out port are positioned so as to face each other;
the fluid outlet of the second chamber and the introduction port are positioned so as to face each other;
the first line is positioned on the device main body along a first side of the filter housing; and
the second line is positioned on the device main body along a second side of the filter housing opposite the first side,
wherein the first line comprises:
an introduction extension portion extending from the introduction port toward the lead-out port, an extending end of the introduction extension portion being positioned closer to the lead-out port than the filter housing; and
an introduction turn portion which curves from the extending end of the introduction extension portion and extends to the fluid inlet, and
wherein the second line comprises:
a lead-out extension portion extending from the lead-out port toward the introduction port, an extending end of the lead-out extension portion being positioned closer to the introduction port than the filter housing; and
a lead-out turn portion which curves from the extending end of the lead-out extension portion and extends to the fluid outlet.

10. The biological component separation device according to claim 9, wherein in a state in which the device main body is suspended, the fluid inlet is positioned at a lower end of the filter housing.

11. The biological component separation device according to claim 10, wherein in the state in which the device main body is suspended, the fluid outlet is positioned at an upper end of the filter housing.

12. The biological component separation device according to claim 9, wherein:
the device main body extends in one direction;
the introduction port is disposed at one end portion of the device main body;
the lead-out port is disposed at another end portion of the device main body; and
the fluid inlet is positioned closer to the lead-out port than the fluid outlet.

13. The biological component separation device according to claim 9, wherein the introduction port, the fluid inlet, the fluid outlet, and the lead-out port are arranged on a same straight line along a longitudinal direction of the device main body.

14. The biological component separation device according to claim 9, wherein the first line and the second line extend in a longitudinal direction of the device main body.

15. The biological component separation device according to claim 9, wherein:
the device main body is formed by mutually joining together a first sheet and a second sheet in a state of being superimposed on one another in a thickness direction, the first sheet and the second sheet being made of the soft material; and
the filter housing, the first line, and the second line are formed between the first sheet and the second sheet.

16. The biological component separation device according to claim 9, wherein the filter member comprises:
a filter main body; and
a support sheet joined in a liquid-tight manner to an outer edge portion of the filter main body so as to encircle the filter main body, and
wherein an outer edge portion of the support sheet is joined in a liquid-tight manner to the device main body.

17. A biological component separation device that separates a predetermined biological component from a biological fluid, the biological component separation device comprising:
a device main body formed of a soft material in a sheet-like shape;
a filter housing in the device main body forming an internal space having a fluid inlet and a fluid outlet;
a filter member configured to partition said internal space into a first chamber and a second chamber, and to capture the predetermined biological component;
an introduction port disposed in the device main body and configured to introduce the biological fluid;
a lead-out port disposed in the device main body and configured to deliver out the biological fluid;
a first line formed in the device main body that connects the fluid inlet provided in the first chamber to the introduction port; and
a second line formed in the device main body and that connects the fluid outlet provided in the second chamber to the lead-out port,
wherein the first line comprises:
an introduction extension portion extending from the introduction port toward the lead-out port, an extending end of the introduction extension portion being positioned closer to the lead-out port than the filter housing; and
an introduction turn portion which curves from the extending end of the introduction extension portion and extends to the fluid inlet,
wherein the second line comprises:
a lead-out extension portion extending from the lead-out port toward the introduction port, an extending end of the lead-out extension portion being positioned closer to the introduction port than the filter housing; and a lead-out turn portion which curves from the extending end of the lead-out extension portion and extends to the fluid outlet, and wherein, in a plan view, a straight section of the introduction extension portion and a straight section of the lead-out extension portion are on opposite sides of the filter housing.

\* \* \* \* \*